United States Patent
Lilienfeld et al.

(10) Patent No.: US 7,111,496 B1
(45) Date of Patent: Sep. 26, 2006

(54) METHODS AND APPARATUS FOR MONITORING A MASS CONCENTRATION OF PARTICULATE MATTER

(76) Inventors: Pedro Lilienfeld, 28 Demar Rd., Lexington, MA (US) 02420; Hansgerd Kramer, Amselfeld 34, 91056, Erlangen (DE)

( * ) Notice: Subject to any disclaimer, the term of this patent is extended or adjusted under 35 U.S.C. 154(b) by 126 days.

(21) Appl. No.: 10/837,393

(22) Filed: Apr. 29, 2004

(51) Int. Cl.
*G01N 37/00* (2006.01)
*G01N 21/00* (2006.01)

(52) U.S. Cl. .................... 73/28.01; 73/24.03; 356/338
(58) Field of Classification Search .............. 73/28.01, 73/24.03; 356/338, 336, 335, 339, 340, 337, 356/72
See application file for complete search history.

(56) References Cited

U.S. PATENT DOCUMENTS

| | | | |
|---|---|---|---|
| 3,177,757 A * | 4/1965 | Polanyi ................... 356/41 |
| 3,266,291 A * | 8/1966 | King, Jr. ................ 73/24.06 |
| 3,879,992 A * | 4/1975 | Bartera ................. 73/24.01 |
| 4,017,193 A * | 4/1977 | Loiterman ............... 356/435 |
| 4,710,887 A * | 12/1987 | Ho ....................... 702/24 |
| 4,827,760 A * | 5/1989 | Saito .................... 73/28.01 |
| 5,349,844 A | 9/1994 | Lilienfeld .............. 73/28.01 |
| 5,434,667 A * | 7/1995 | Hutchins et al. .......... 356/338 |
| 5,483,080 A * | 1/1996 | Tam ....................... 250/574 |
| 6,055,052 A | 4/2000 | Lilienfeld ............... 356/338 |
| 6,496,258 B1 * | 12/2002 | Leipertz et al. ........... 356/336 |
| 6,955,787 B1 * | 10/2005 | Hanson .................... 422/50 |
| 2004/0066512 A1 * | 4/2004 | Politze et al. ............ 356/338 |
| 2004/0233431 A1 * | 11/2004 | Ganz et al. .............. 356/338 |

OTHER PUBLICATIONS

Lilienfeld, P., "Method for Continuous Monitoring of Particulates as Applied to the $PM_{10}$ Standard", Quality Assurance in Air Space Pollution Measurement, Transactions, pp. 63-80, Oct. 1984.

* cited by examiner

*Primary Examiner*—Michael Cygan
(74) *Attorney, Agent, or Firm*—Barry W. Chapin, Esq.; Chapin IP Law, LLC

(57) ABSTRACT

A particulate mass monitor includes two mass sensors, such as an optical sensor (e.g., a light scattering photometer or nephelometer) and a beta radiation attenuation sensor for substantially continuous monitoring of ambient particulate matter. During operation, the first mass sensor references the time-averaged measurement of the second mass sensor such that the second mass sensor calibrates the response of the first mass sensor. If the first sensor is an optical sensor, as it detects the presence of particulate matter within a fluid, the mass concentration measurement (e.g., signal output) provided by the optical sensor is altered using a ratio of concentration measurements of the second mass sensor and the optical sensor. The combined use of the two mass sensors provides accurate mass measurements of ambient particulate matter with a relatively high time resolution.

41 Claims, 8 Drawing Sheets

METHODS AND APPARATUS FOR MONITORING A MASS CONCENTRATION OF PARTICULATE MATTER

FIELD OF THE INVENTION

Embodiments of the present invention relate generally to a system and method for measuring and monitoring the mass concentration of airborne particles.

BACKGROUND

Ambient air quality affects the health of people breathing the ambient air. The lower the air quality, the greater the risk for health-related problems induced by the ambient air. Conventional particulate matter monitoring devices measure the mass concentration of particulate matter within ambient air, gases, or other fluids to determine quality of the ambient air or gaseous fluid. A conventional particulate matter monitoring device can provide a warning to a user when the device detects a relatively low air quality (e.g., a relatively large particulate mass concentration within the air) or a decrease in the ambient air quality based upon an increase in particulate mass concentration measured over a specific time period.

Several sensing techniques provide continuous direct monitoring of airborne particulate mass concentration. The sensing techniques used for particulate monitoring include, for example, mass sensing methods such as beta radiation attenuation and optical sensing methods such as light scattering photometry or nephelometry.

Beta radiation attenuation devices typically include a mass sensing stage and a particle collection stage. The mass sensing stage includes a beta particle radiation source, typically carbon-14 or krypton-85, and a beta radiation detector, typically a Geiger-Muller detector, plastic scintillator, a proportional counter, or an ionization chamber. The particle collection stage includes a filter oriented between the beta radiation source and the beta radiation detector. Beta radiation attenuation devices exhibit a substantially exponential attenuation characteristic as a function of the mass per unit area collected by the filter between the radiation source and the radiation detector. For example, during operation, ambient air (or another gaseous compound) flows through the filter and the filter collects particulate matter present within the ambient air over time. As the amount of particulate matter collected by the filter increases, the particulate matter attenuates the beta radiation emitted from the radiation source (i.e., the beta radiation detector senses less radiation from the beta source) as detected by the detector. Because the attenuation of the beta radiation detected by the beta detector is related to the mass of the particulate matter collected by the filter (e.g., and does not substantially depend upon the type or compound of material collected by the filter), a beta radiation signal produced by the beta radiation attenuation device indicates a mass concentration of particulate matter within an air sample.

Beta radiation attenuation devices, and other mass sensing devices that utilize a filter to collect particulate matter within an air sample, sometimes utilize temperature and humidity conditioning elements to remove liquid water from the air sample. Typically, air samples include varying amounts of water and water vapor. If the filter collects water over time, the water adds to the attenuation of the beta radiation from the beta radiation source to the beta detector. The water that collects in the filter, therefore, can affect the accuracy of the device's detection of mass of particulate matter within the air sample. In conventional beta radiation attenuation devices, prior to the air sample reaching the filter, the device heats the air sample to ensure that the water in the air and on the particulate matter evaporate from the air sample. By keeping the water within the air sample as a vapor instead of condensation, the temperature and humidity conditioning elements can increase the particulate matter detection accuracy of the device by reducing or eliminating collection of water in the filter.

Another type of conventional particulate mass sensing device is a light scattering device known as a nephelometer. Light scattering photometry devices, such as nephelometers, measure the irradiance of light scattered by particles passing through a sensing volume. Typical light scattering photometry devices include a light source that creates an illuminating light beam and detection optics or sensors that measure the strength of the scattered light. During operation, ambient air or another gas flows through a sensing volume defined by an intersection of the illuminating beam and the field of view of the sensing optics. As the air flows through the sensing volume, the light source illuminates particles present within the sensing volume, and the optics and associated photosensitive measuring circuitry detect the light scattered by the particles. For an ambient air sample having a fixed size distribution of particles with invariant density and index of refraction, the intensity of light scattered by the particles within the air sample is directly proportional to the mass concentration of the particles within the air sample. Light scattering photometry or nephelometry devices, therefore, allow real-time (i.e., substantially instant) measurement of particulate mass concentration of ambient air.

SUMMARY

Conventional mechanisms and techniques that provide monitoring of airborne particulate mass concentration levels suffer from a variety of deficiencies.

As indicated above, in mass sensing methods for particulate monitoring, such as performed using beta radiation attenuation devices, attenuation of the beta radiation depends substantially upon the mass of the material collected by the filter and does not substantially depend upon the type or compound of material collected by the filter. Thus, a beta radiation signal produced by the beta radiation attenuation device indicates a mass concentration of particulate mater within an air sample. Beta radiation attenuation devices typically provide reliable measurements of particulate mass concentration over relatively long time periods (e.g., periods of several hours). However, when conventional beta radiation attenuation devices are used for particulate monitoring over relatively short periods of time (less than a few hours) or in the presence of a relatively low particulate concentration within an air sample, statistical noise inherent in the beta radiation counting method limits accurate quantification of particulate mass concentrations.

Additionally, conventional beta radiation attenuation devices typically utilize temperature and humidity conditioning elements to remove or vaporize liquid water from an air sample. The conditioning elements help to minimize the effect of liquid water within the air sample on the detection accuracy of the beta radiation attenuation devices. However, ambient air samples can include volatile particulate matter. When a beta radiation attenuation device heats an incoming air stream having volatile particulate matter, the device diminishes the relative humidity of the air sample and also can evaporate the volatile particulate matter. As a result, more than minimal heating can decrease the detection accuracy of the conventional beta radiation attenuation device.

Also, as indicated above, light scattering photometry or nephelometry devices allow real-time (i.e., substantially instant) measurement of particulate mass concentration of ambient air. Nephelometers perform time resolved particulate mass concentration measurements with minimal noise. Such measurements provide relatively low mass concentration sensing (e.g., allows detection of single particles). However, particle size, particle shape, and a particle's refractive index may influence measurements taken by nephelometers. In view of this, and since light scattering photometry measurements are not substantially dependent on a particle's density (i.e., the specific gravity of the particle), particles having different masses can produce the same light scattering effect within a nephelometer. Conventional nephelometry measurements of particle mass can therefore be somewhat inaccurate.

By contrast, embodiments of the present invention significantly overcome the described deficiencies and provide mechanisms and techniques for monitoring a mass concentration of particulate matter within a fluid. A particulate mass monitor configured in accordance with embodiments of the invention includes a first type of particulate mass sensing detector or device, such as an optical sensor (e.g., a light scattering photometer), coupled with a second type of mass sensing device, such as a beta radiation attenuation sensor with the two devices operating in conjunction with each other to provide a more accurate measurement of mass of particulate matter in a sample volume (e.g., air, gas, or other fluid). During operation, the first sensing device (e.g., the optical sensor or nephelometer) references the time-averaged measurement of the second mass sensing device (e.g., the beta radiation attenuation sensor) such that the second mass sensing device calibrates the response of the first mass sensing device.

In one embodiment, the first sensing device is an optical sensor and the second sensing device is a mass sensing radiation device. Alternatively, the second sensor is a mechanical resonance sensing assembly such as an oscillating filter type mass sensing device. Accordingly, the second sensor is referred to generally herein as a mass sensing detector, whereas the first sensing device is referred to herein as the optical sensor. In operation of one embodiment, the optical sensor detects the presence of particulate matter within a fluid, and the beta-based mass sensing device alters the mass concentration measurement (i.e., signal output) provided by the optical sensor. The combined use of the beta-based mass sensing device and the optical-based mass sensor provides substantially accurate mass measurements of ambient particulate matter with a relatively high time resolution of the order of minutes or even seconds, as compared to several hours for a conventional beta radiation attenuation based monitor.

In one arrangement, a particulate mass monitor receives a fluid sample, detects a first mass concentration of particulates within the fluid sample using an optical sensor, and detects a second mass concentration of particulates within the fluid sample using a mass sensing device. The particulate mass monitor then determines a final mass concentration level of particulates within the fluid sample by multiplying the real-time optical sensor signal with a ratio between the second mass concentration and the first mass concentration measurements. The particulate mass monitor, therefore, calibrates the response of the optical sensor using the particulate mass concentration detected by the mass sensing device, i.e., inaccuracies of the particulate mass concentration measurements of the optical sensor are reduced or corrected using the relatively accurate particulate mass concentration measurements of the mass sensing device.

In one arrangement, the particulate mass monitor receives, in a substantially continuous manner, first mass concentration values of particulates within the fluid sample from the optical sensor and averages, in a substantially continuous manner, the first mass concentration values over a time interval to generate a first average mass concentration value of particulates within the fluid sample. Additionally, the particulate mass monitor receives, in a substantially continuous manner, second mass concentration values of particulates within the fluid sample from the mass sensing device and averages, in a substantially continuous manner, the second mass concentration values over the time interval to generate a second average mass concentration value of particulates within the fluid sample. By continuously averaging the first particulate mass concentration values and the second particulate mass concentration values over the time interval, the particulate mass monitor provides a running correction to the final mass concentration level of particulates within the fluid.

In one arrangement, the particulate mass monitor detects a rate of change of the first mass concentration of the fluid sample. Depending on the rate of change of the mass concentration measured by the optical sensor, the particulate mass monitor then adjusts the time interval for averaging the first mass concentration of particulates within the fluid sample and for averaging the second mass concentration of particulates within the fluid sample. Such adjustment affects the ratio calculated by the particulate mass monitor and allows the particulate mass monitor to produce a relatively accurate final mass concentration value of the particulates within the fluid sample, regardless of variations in particulate properties such as density, size, shape, or refractive index within the air sample.

In one arrangement, the particulate mass monitor detects a relative humidity level of the fluid sample and compares the relative humidity level of the fluid sample with a threshold humidity value. When the relative humidity level of the fluid sample reaches the threshold value, the particulate mass monitor heats the fluid sample prior to detecting the second mass concentration of particulates within the fluid sample. Such heating maintains the humidity level within the fluid sample below a critical level that minimizes the amount of liquid water collected by the mass sensing device over time and minimizes evaporation of volatile particulate matter within the fluid sample as typically caused by heating the fluid sample.

In one arrangement, the particulate mass monitor, when determining the final mass concentration level of particulates within the fluid sample, compares the second mass concentration with a second mass concentration threshold value. When the mass sensing detector operates for a minimal time period or the fluid sample contains a relatively low or near zero particulate concentration, the second mass concentration does not reach the second mass concentration threshold value. As such, the particulate mass monitor ignores the ratio between the second and first mass concentration measurements and reports the instant, optically measured mass concentration measurement as the final mass concentration level of particulates within the fluid sample. The particulate mass monitor minimizes the effect of potentially inaccurate mass sensing detector measurements on the instant mass concentration measurements taken by the optical sensor.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Embodiments of the present invention provide mechanisms for monitoring a mass concentration of particulate matter within a fluid. A particulate mass monitor includes a mass sensing device, such as a beta radiation attenuation sensor, and an optical sensor, such as a light scattering photometer (i.e., nephelometer) for substantially continuous monitoring of ambient particulate matter. During operation, the optical sensor references the time-averaged measurement of the mass sensing device such that the mass sensing device calibrates the response of the optical sensor. As the optical sensor detects the presence of particulate matter within a fluid, the mass sensing device alters the mass concentration measurement (e.g., signal output) provided by the optical sensor. The combined use of the mass sensing device and the optical sensor provides substantially accurate mass measurements of ambient particulate matter with a relatively high time resolution on the order of minutes, or even seconds.

Figure 1:
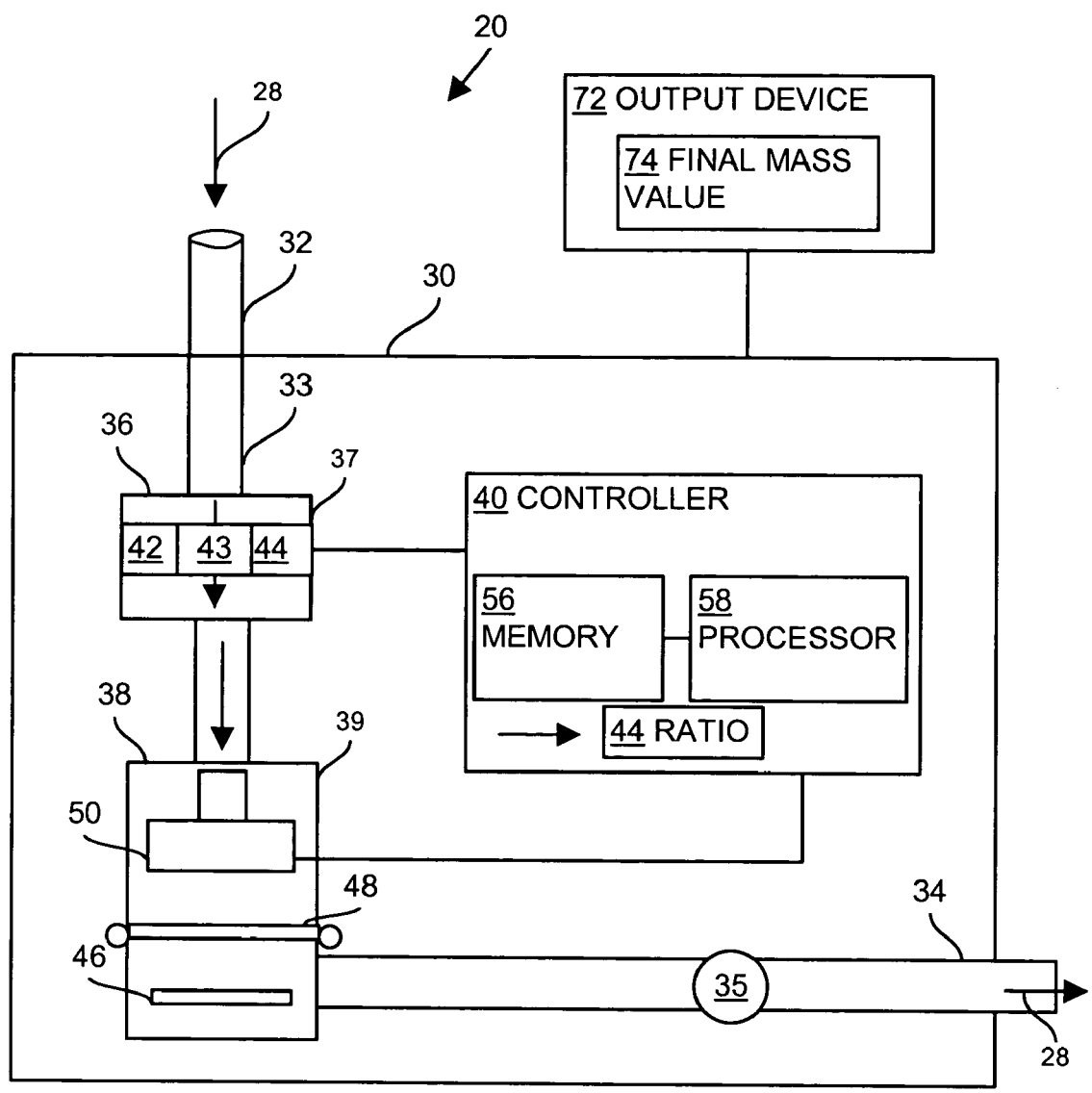
FIG. 1 illustrates a particulate mass monitor, according to one embodiment of the invention.

FIG. 1 shows a particulate mass monitor 20, according to one arrangement. The particulate mass monitor 20 includes a housing 30 having a fluid inlet 32, a fluid outlet 34, a first sensor, such as an optical sensor 36 or other relatively fast particulate sensor, a second sensor, such as a mass sensing device or mass detector 38, a controller 40, and an output device 72. The particulate mass monitor 20 is configured to monitor a fluid sample 28, such as a gas or air sample, from a fluid source for particulate matter (PM), such as within $PM_{10}$ (i.e., particulate matter having a size smaller than 10 micrometers), or $PM_{2.5}$ (i.e., particulate matter having a size smaller than 2.5 micrometers) particle size ranges. The particulate mass concentration of the fluid sample relates to the particulate mass concentration of the fluid source. For example, as the particulate mass monitor 20 continuously receives an air sample from an ambient air source, detection of a particulate mass concentration within the air sample generally relates to the particulate mass concentration of the ambient air source.

The fluid inlet 32 and fluid outlet 34 are configured to direct fluid through the particulate mass monitor 20. For example, the fluid inlet 32 and fluid outlet 34 include a channel 33 through the housing 30 of the particulate mass monitor 20 that provides fluid communication among the fluid inlet 32, the optical sensor 36, the mass sensing detector 38, and the fluid outlet 34. The monitor 20, in one arrangement, has a pump 35 external to the fluid outlet 34 that is configured to maintain a substantially constant flow rate of fluid through the particulate mass monitor 20.

The optical sensor 36 positions between the fluid inlet 32 and the mass sensing detector 38 and is configured to provide real-time (e.g., substantially instant) measurement of particulate mass concentration within the fluid sample 28. The optical sensor 36 defines a chamber 37 having a source 42 and a detector 44 configured to measure the irradiance of light scattered by particles (e.g., particulate matter within the air sample 28) passing through a sensing volume 43 defined by the source 42 and the detector 44. In one arrangement, the optical sensor 36 is configured as a light scattering photometer, such as a nephelometer. In such an arrangement, the source 42 includes, for example, a referenced stabilized, pulsed, near-infrared light emitting diode with a high output operating at a center wavelength of approximately 880 nm. The detector 44, in turn, utilizes synchronous detection of the pulsed wave to maximize signal stability and minimize external noise. The optical sensor 36 is similar to that incorporated in the inline nephelometer model HPM-1000, manufactured by Thermo Electron Corporation of Waltham, Mass.

The mass sensing device 38 couples to the channel 33 at a position distal to (i.e., downstream from) the optical sensor 36 and is configured to measure a particulate mass concentration within the fluid sample 28. In one arrangement, the mass sensing device 38 is configured as a beta radiation attenuation assembly, such as beta gauge model FH62-C14, manufactured by Thermo Electron Corporation of Waltham, Mass. In such an arrangement, the beta radiation attenuation assembly 38 defines a chamber 39 having a radiation source 46, a filter 48 such as a filter collection tape, and a radiation detector 50 opposing the radiation source 46. In one arrangement, the radiation source 46 is a carbon-14 (C-14) beta source having an activity of approximately 100 microcuries. The C-14 source provides a relatively low energy beta radiation and has a relatively long half-life (i.e., approximately 5700 years).

The controller 40 electrically couples to, and is configured to receive signals from, both the optical sensor 36 and the mass sensing device 38. The controller includes a memory 56 and a processor 58. The memory 56 can be volatile or non-volatile memory or a storage system such as a computer memory (e.g., random access memory (RAM), read only memory (ROM), or another type of memory) disk memory, such as hard disk, floppy disk, optical disk, for example. The processor 58 can be circuitry or a processing device such as a central processing unit, controller, application specific integrated circuit, programmable gate array, or other circuitry.

The output device 72 couples to the particulate mass monitor 20 and is configured to indicate a particulate mass concentration associated with the fluid sample 28 as measured by the particulate mass monitor 20. In one arrangement, the output device 72 is configured as a display, such as a liquid crystal display or a light emitting diode display. In another arrangement, the output device 72 is configured as a digital data output port.

During operation the controller 40 receives signals from mass sensing device 38 and the optical sensor 36 indicating particulate mass concentrations within the fluid sample 28. The controller computes a ratio of the signals and applies the ratio 44 to real-time particulate mass concentration measurements made by the optical sensor 36.

Figure 2:
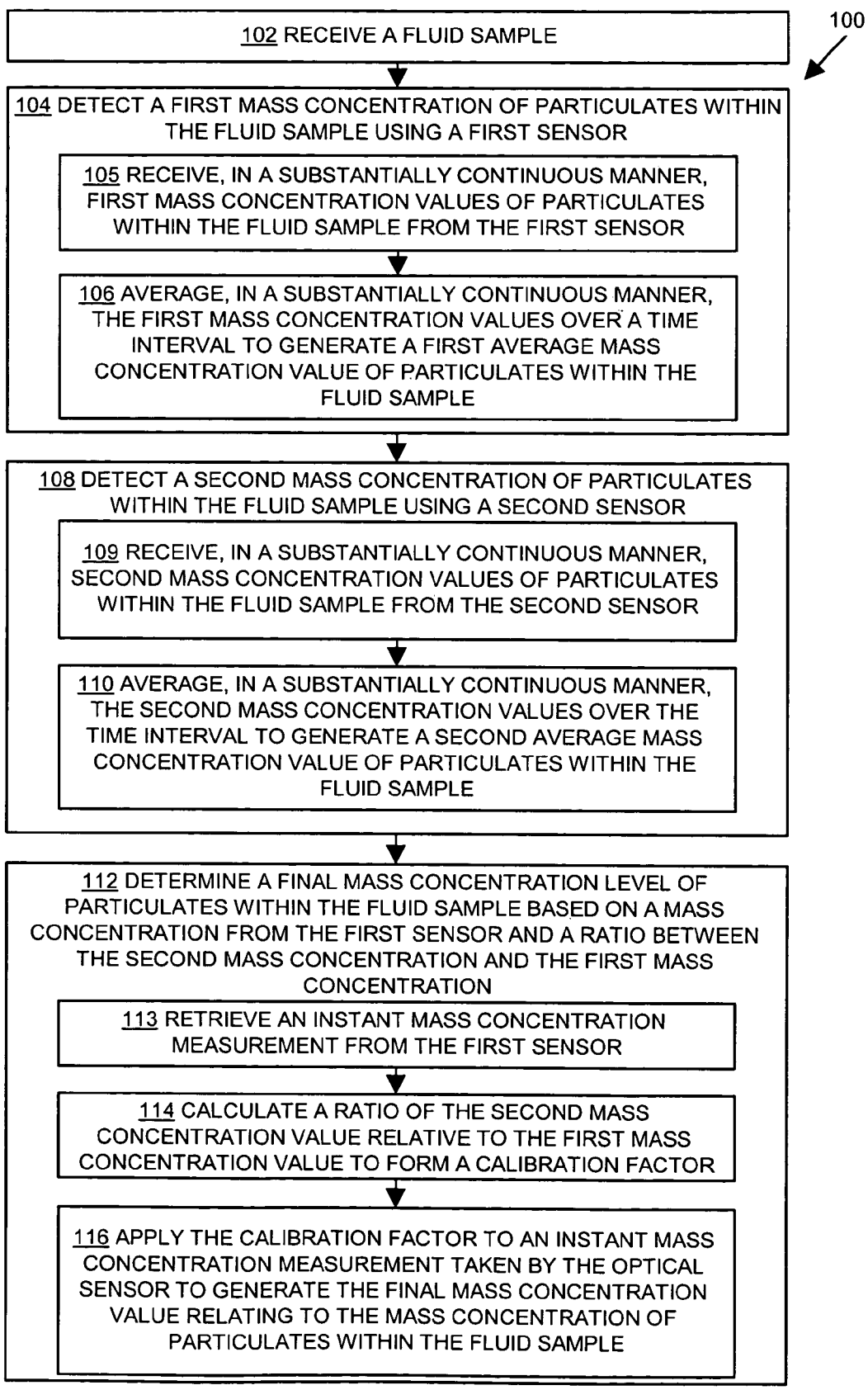
FIG. 2 illustrates a flow chart of a procedure performed by the particulate mass monitor of FIG. 1, according to one embodiment of the invention.

FIG. 2 is a flow chart 100 of a procedure performed by the particulate mass monitor 20. During the procedure, the controller 40 adjusts particulate matter concentration measurements taken by the optical sensor 36 to agree with particulate matter concentration measurements taken by the mass sensing device 38. By adjusting the measurements taken by the optical sensor 36 the controller 40 combines the relative speed of particulate mass concentration associated with the optical sensor 36 with the accuracy of particulate mass concentration associated with the mass sensing device 38.

In step 102, the particulate mass monitor 20 receives a fluid sample 28. For example, in one arrangement, the pump 35 generates a pressure differential between the fluid inlet 32 and the fluid outlet 34 to cause a fluid sample 28 to enter the particulate mass monitor 20 via the fluid inlet 32. In the case where the fluid inlet 32 and the fluid outlet 34 are open to the atmosphere, the pump 35 causes ambient air 28 to enter the fluid inlet 32 of the particulate mass monitor 20.

In step 104, the controller 40 detects a first mass concentration of particulates within the fluid sample 28 using a first sensor, such as the optical sensor 36. For example, the fluid inlet 32 directs the ambient air sample 28 to the optical sensor 36 such that the ambient air sample 28 flows within a sensing volume 43 defined by the source 42 and the detector 44. Assume that the ambient air sample 28 includes particulate matter. During operation, the source 42 illuminates the sensing volume 43. The particulate matter within the air sample (e.g., the particulate matter located within the sensing volume) causes the light to scatter. The detector 44 detects the scattered light from the particulate matter and, in turn, generates a voltage output signal proportional to the detected irradiance. The controller 40 receives the output signal from the optical sensor 36 (e.g., from the receiver 44) as an indication of the mass concentration of particulates within the fluid sample 28.

In step 108, the controller 40 detects a second mass concentration of particulates within the fluid sample using a second sensor, such as the mass sensing device 38. For example, during operation, the channel 33 of the particulate mass monitor 20 carries the air sample 28 from the optical sensor 36 to the mass sensing device 38. In the case where the mass sensing device 38 is configured as a beta radiation attenuation sensing assembly, particulate matter within the air sample 28 collects on the filter 48. As the amount of particulate matter collected by the filter 48 increases, the collected particulate matter attenuates the beta radiation emitted from the radiation source 46 and detected by the radiation detector 50. The beta radiation detector 50 transmits a signal to the controller 40 proportional to the mass concentration of particulates within the fluid sample 28.

In step 112, the controller 40 determines a final mass concentration level of particulates within the fluid sample 28 based on a mass concentration from the first sensor 36 and a ratio 44 between the second mass concentration and the first mass concentration. The controller 40 utilizes the ratio 44 to adjust real time particulate mass concentration measurements taken by the optical sensor 36, as described below.

In step 113, the controller 40 retrieves an instant mass concentration measurement from the first sensor 36. During operation, the optical sensor 36 continuously detects the particulate mass concentration of particulate matter within air 28 entering the particulate mass monitor 20. The controller 40 averages the continuously detected mass concentration measurements taken by the optical sensor 36 over a preset period, such as a period of approximately one minute. The one-minute average particulate mass concentration forms an "instant" mass concentration measurement of the air 28 entering the particulate mass monitor 20.

In step 114, in one arrangement, the controller 40 calculates the ratio 44 of the second mass concentration value relative to the first mass concentration value to form a calibration factor. For example, the controller 40 divides the mass concentration of particulates measured by the beta radiation attenuation sensing assembly (i.e., the second mass concentration value) by the mass concentration of particulates measured by the light scattering photometer (i.e., the first mass concentration value) to calculate the ratio 44.

In step 116, the controller 40 applies the calibration factor (i.e., the ratio 44) to the instant mass concentration measurement taken by the optical sensor 36 to generate the final mass concentration value 74 relating to the mass concentration of particulates within the fluid sample 28. When applying the ratio 44 to the mass concentration measurement taken by the optical sensor 36, the controller 40 multiplies the ratio 44 and the one-minute average particulate mass concentration (i.e., the "instant" mass concentration) from the optical sensor 36 to generate the final (i.e., corrected) mass concentration value.

Application of the ratio 44 to the "instant" particulate mass concentration measured by the optical sensor 36 calibrates the response of the optical sensor 36 with respect to the particulate mass concentration in a fluid (e.g., air) sample as detected by the mass sensing device 38. For example, as indicated above, different types of particulate matter, having relatively different densities or masses, produce similar light scattering effects within the optical sensor 36. Hence, the optical sensor 36 can provide inaccurate measurement of particulate mass concentrations within a fluid sample because the measurements taken by the optical sensor 36 do not substantially depend upon the density of the particulate matter. Measurements made by mass sensing device 38, however, depend upon the density or mass of the particulate matter within a fluid sample 28 and provide relatively accurate measurement of particulate mass concentrations within a fluid sample. By applying the ratio 44 to the particulate mass concentration measurements taken by the optical sensor 36, the controller 40 adjusts for inaccuracies of the optical sensor 36. The monitor 20, therefore, combines the relative speed of particulate mass concentration sensing associated with the optical sensor 36 (e.g., nephelometer) with the accuracy of particulate mass concentration sensing associated with the mass sensor 38 (e.g., beta radiation attenuation sensing assembly).

FIG. 2 also illustrates additional steps performed by the controller 40 when detecting a first mass concentration of particulates within the fluid sample 28 using the optical sensor 36 (step 104) and detecting a second mass concentration of particulates within the fluid sample using the mass sensor 38 (step 108).

In step 105, in one arrangement, when detecting the first mass concentration, the controller 40 receives in a substantially continuous manner, first mass concentration values of particulates within the fluid sample from the first sensor, such as the optical sensor 36. Additionally in step 109, in one arrangement, when detecting the second mass concentration, the controller 40 receives, in a substantially continuous manner, second mass concentration values of particulates within the fluid sample from the second sensor such as the mass sensor 38.

During operation, for example, the pump 35 causes fluid to flow from an external source (e.g., ambient air) through the fluid inlet 32 and toward the fluid outlet 34 at a substantially constant flow rate. The optical sensor 36 continuously detects the presence of particulate matter within the fluid (e.g., the fluid sample) and provides a real-time measurement of particulate mass concentration within the fluid sample 28 to the controller 40 at a preset rate. The mass sensor 38 also continuously measures the particulate mass concentration (e.g., based on beta radiation attenuation) within the fluid sample 28 as the filter 48 of the mass sensor 38 collects particulate matter present within the fluid sample 28. The mass sensor 38 also provides a measurement of particulate mass concentration within the fluid sample 28 to the controller 40 at a preset rate.

In step 106, the controller 40 averages, in a substantially continuous manner, the first mass concentration values over a time interval to generate a first average mass concentration value of particulates within the fluid sample 28. Also, in step 110, the controller 40 averages, in a substantially continuous manner, the second mass concentration values over the time interval to generate a second average mass concentration value of particulates within the fluid sample 28.

By continuously averaging the first particulate mass concentration values and the second particulate mass concentration values over the given time interval, the controller 40 provides a running correction to the final mass concentration level of particulates within the fluid. For example, the controller 40 calculates the calibration value or ratio 44 using the first average mass concentration value and the second average mass concentration value, taken at any instant within the time interval. The controller 40 then applies the ratio 44 to a corresponding instantaneous particulate mass concentration measurement taken by the optical sensor 36. As the controller 40 continuously updates the ratio 44 (i.e., by continuously receiving and averaging particulate mass concentration values), in the case where the particulate mass concentration of a fluid sample changes relatively quickly over the time interval, the controller 40 can adjust the instantaneous particulate mass concentration measurement taken by the optical sensor 36 in a substantially rapid or real-time manner.

In steps 106 and 110, as described above, the controller 40 averages the first and second mass concentration values over a time interval to generate first and second average mass concentration value of particulates within the fluid sample 28, respectively. Over time, however, the particulate mass concentration of air 28 entering the particulate mass monitor 20 can change. Based upon a detected change in the particulate mass concentration of an air sample 28 over time, in one arrangement, the controller 40 adjusts the time interval for averaging the first and second mass concentrations of particulates within the fluid sample 28.

Figure 3:
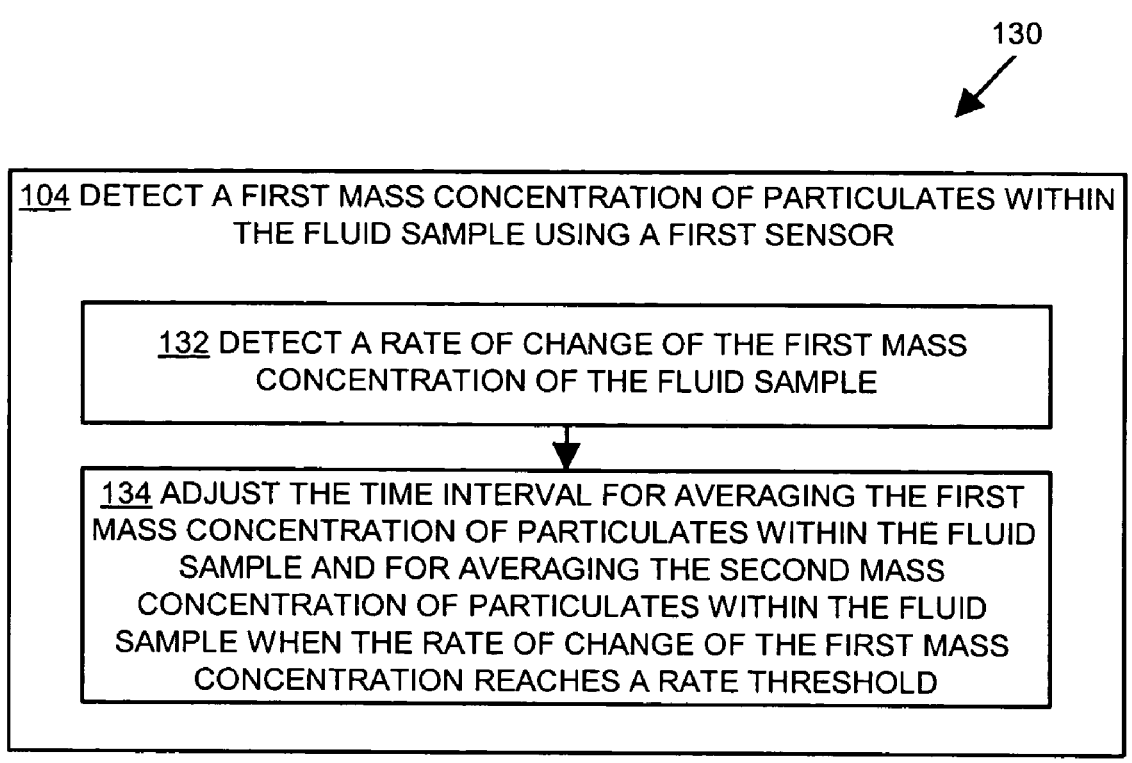
FIG. 3 illustrates a flow chart of a procedure performed by the particulate mass monitor of FIG. 1, according to one embodiment of the invention.

FIG. 3 is a flow chart 130 of a procedure performed by the controller 40 of the particulate mass monitor 20 to account for changes in particulate mass concentration of an air sample over time, for example.

In step 104, as indicated above, the controller 40 detects the first mass concentration of particulates within the fluid sample 28 using the first sensor 36. For example, during operation, the controller 40 receives an output signal from the optical sensor 36 (i.e., from the receiver 44) as an indication of the mass concentration of particulates within the fluid sample 28.

In step 132, the controller 40 detects determines a rate of change of the first mass concentration of the fluid sample 28. For example, as the optical sensor 36 continuously provides the output signal to the controller 40, the controller 40 subtracts a latest (i.e. most recently received) output signal from the optical sensor 36 from an earlier (i.e., previously received) output signal and divides the result by a time span between the earlier received output signal and the latest received output signal. The resulting value represents the rate of change of the first mass concentration within the fluid sample 28.

In step 134, the controller 40 adjusts the time interval for averaging the first mass concentration of particulates within the fluid sample 28 and for averaging the second mass concentration of particulates within the fluid sample 28 when the rate of change of the first mass concentration reaches a rate threshold. When the controller 40 detects the rate of change of the first mass concentration has reached (e.g., approaches) the rate threshold (i.e., the rate of change is substantially equal to or greater that the rate threshold), the controller 40 attributes this to a change such as an increase in the particulate mass concentration of the fluid sample 28 or a change in the characteristics of the particulates within the fluid sample. The controller 40 then adjusts the time interval for averaging the first and second mass concentrations of particulates within the fluid sample 28. Such adjustment affects the ratio 44 calculated by the controller 40 and allows the controller to produce a relatively accurate final mass concentration value of the particulates within the fluid sample 28, regardless of variations in particulate mass concentration within the air sample 28.

For example, assume the controller 40 detects a substantially constant particulate mass concentration within the air sample using the optical sensor 36. In such a case, the size distribution of the particulate matter, the index of refraction of the particulate matter, and the source or type of particulate matter, as measured by optical sensor 36, are substantially constant and the rate of change of the mass concentration of the particulates is substantially low. Further assume that the rate threshold is set at a relatively high value. In such a case, when the controller 40 compares the rate of change of the mass concentration of the particulates to the rate threshold, the controller 40 determines that the rate of change of the mass concentration of the particulates is lower than the rate threshold. Based upon the results of the comparison, the controller 40 then averages the first and second mass concentrations of particulates within the fluid sample 28 over a relatively large time interval (e.g., up to approximately 12 hours). Because mass sensors 38 (e.g., beta radiation attenuation devices) typically provide reliable measurements of particulate mass concentration over relatively long time periods (e.g., periods of several hours), by using a relatively large time interval for averaging, the controller 40 provides a relatively accurate final mass concentration value relating to the mass concentration of particulates within the fluid sample 28.

In another example, assume the controller 40 detects an increase in the particulate mass concentration within the air sample 28, as measured using the optical sensor 36. Typically, an increase in a particulate concentration gradient within a fluid sample 28, as measured by the optical sensor 36, indicates a change in the properties of the particulates, such as particulate size characteristics, within the air sample 28 (e.g., particulate size characteristics typically influence a relationship between particulate light scattering and mass concentration of the particulates within the air sample 28). In such a case, when the controller 40 compares the rate of change of the mass concentration of the particulates to the rate threshold, the controller 40 determines that the rate of change of the mass concentration of the particulates is substantially equal to or is greater than (i.e., the rate of change reaches) the rate threshold. Based upon the results of the comparison, the controller 40 then decreases the averaging time interval and averages the first and second mass concentrations of particulates within the fluid sample 28 over a relatively short time interval (e.g., as short as approximately 2 minutes).

Figure 4:
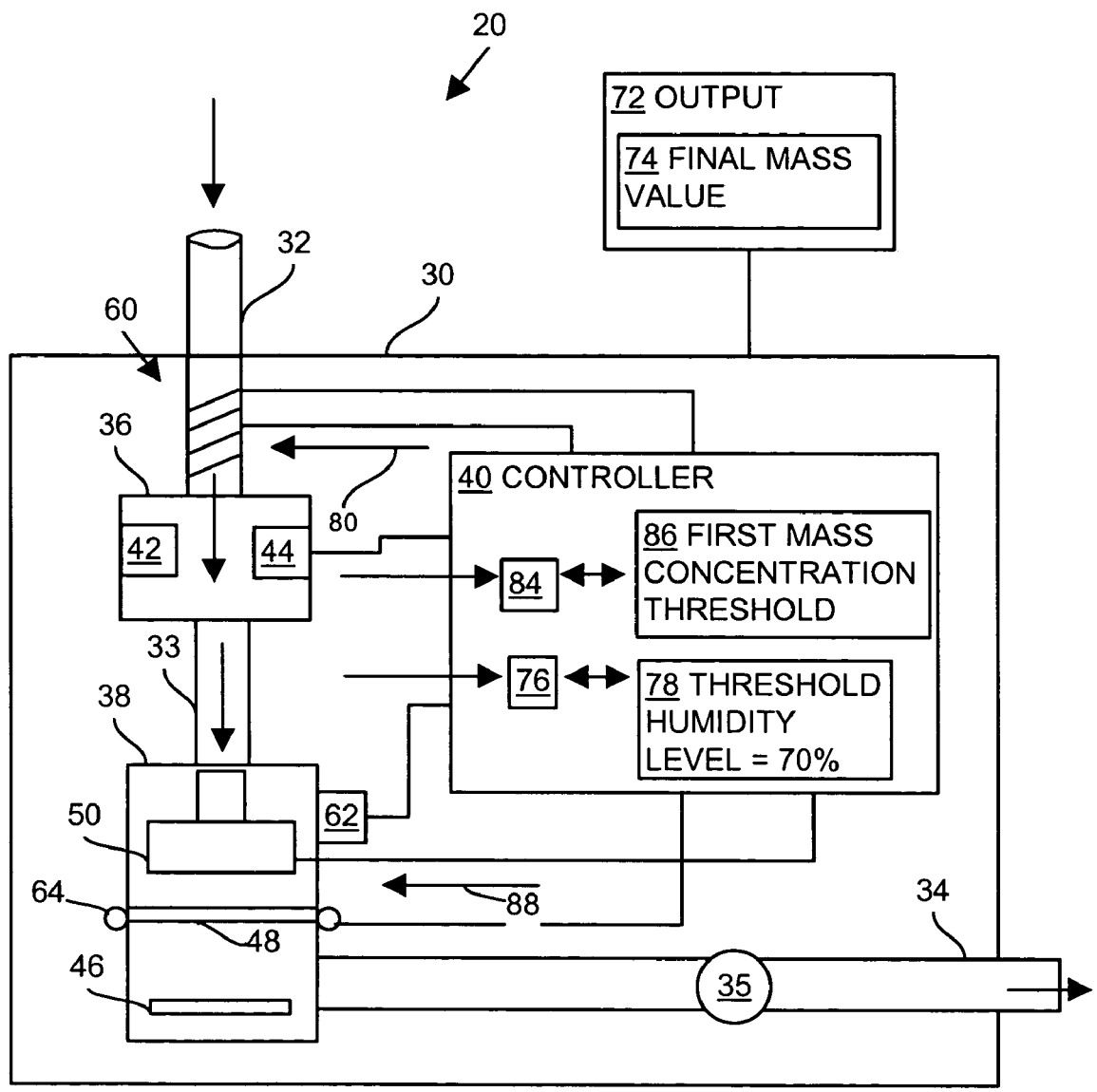
FIG. 4 illustrates an arrangement of a particulate mass monitor, according to one embodiment of the invention.

FIG. 4 illustrates another arrangement of the particulate mass monitor 20. As illustrated, the particulate mass monitor 20 includes a heating element 60, a humidity sensor 62, and a filter advancement mechanism 64 electrically coupled to the controller 40.

The heating element 60, in one arrangement, is attached to a conduit forming the channel 33 at a location between the fluid inlet 32 and the optical sensor 36 and is configured to heat fluid 28, such as an air sample, as it flows toward the optical sensor 36 through the channel 33. As indicated above, fluid 28, such as an air sample, includes varying amounts of water. When the mass sensor 38 is configured as a beta radiation attenuation assembly, as the filter 48 of the mass sensor 38 collects water over time, the water contributes to the attenuation of the beta radiation from the beta particle radiation source 46 to the beta radiation detector 50, thereby affecting the accuracy of the sensor's measurement of a particulate mass concentration within the air sample. During operation, the heating element 60 heats the fluid 28 (e.g., the air sample) contained within the channel 33 (i.e., located between the inlet 32 and the optical sensor 36) to evaporate a portion of the water associated with the fluid 48. The heating element therefore minimizes the effect of water on the particulate mass concentration detected by the mass sensor 38.

The humidity sensor 62 is configured to measure the relative humidity of the fluid 28 within the vicinity of the filter 48 of the mass sensor 38. In one arrangement, the heating element 60 works in conjunction with the humidity sensor 62 to heat the fluid 28, prior to the fluid reaching the filter 48, based on a detected humidity level 76 of the fluid 28. In such an arrangement, the heating element 60 generates enough heat to maintain the humidity within the fluid sample 28 at a particular critical level so as not to "overheat" the sample 28. As indicated above, ambient air samples 28 can include volatile particulate matter. When exposed to excessive heat, the volatile particulate matter evaporates prior to reaching (i.e., being measured by) the mass sensor 38 thereby decreasing the overall detection accuracy of the mass sensor 38. By heating the fluid sample 28 to a temperature (or adjusting the temperature of the fluid sample 28 over time) that maintains the fluid sample 28 at or below a specific humidity level, the heating element 60 and humidity sensor 62 maintain the presence of volatile particulate matter within the fluid sample 28 and increase the accuracy and precision of the particulate mass concentration measurements produced by the mass sensor 38.

During operation, in one arrangement, the controller 40 determines a relative humidity level 76 of the fluid sample 28. For example, the controller 40 receives an electrical signal from the humidity detector 62 indicating the humidity level of the fluid 28. The controller 40 then compares the relative humidity level 76 of the fluid sample 28 with a threshold humidity value 78. For example, in one arrangement, the threshold humidity level is equal to a relative humidity of approximately 70%. Such a humidity level minimizes the amount of water collected by the mass sensor 38 over time and minimizes evaporation of volatile particulate matter within the fluid sample 28.

When the controller 40 determines that the relative humidity level 76 of the fluid sample 28 has reached the threshold value 78, the controller 40 activates the heating element 60 to apply heat 80 to the fluid sample 28 prior to the mass sensor 38 detecting the mass concentration of particulates within the fluid sample 28. In such an arrangement, the controller 40 and heating element 60 apply an amount of heat 80 to the fluid sample 28 sufficient to limit the humidity level within the fluid sample 28 and sufficient to minimize evaporation of volatile particulate matter present within the fluid sample 28. As a result, by controlling heating of the fluid sample 28, the controller 40 allows the mass sensor 38 (e.g., the beta radiation attenuation assembly) to measure the volatile particulate matter within the fluid sample 28. Hence, the controller 40 in conjunction with the heating element 60 and humidity sensor 62 increases the accuracy and precision of the particulate mass concentration measurements produced by the particulate mass monitor 20.

As indicated above, the particulate matter monitor 20 illustrated in FIG. 4 includes a filter advancement mechanism 64 electrically coupled to the controller 40. During operation, the controller 40 actuates the filter advancement mechanism 64 to advance the filter 48 of the mass sensing detector 38 to a "clean" or unused location at a desired advancement rate. When the mass sensor 38 is configured as a beta radiation attenuation sensor, the controller 40 advances the filter 48 to position an unused or "clean" portion relative to the beta source 46 and the radiation sensor 50. Such advancement prevents or limits clogging of the filter 48 over time.

In one arrangement, the controller 40 is configured to advance the filter 48 at a relatively fast or high rate when the optical sensor 36 detects a relatively high particulate mass concentration within the fluid sample 28. For example, in such an arrangement, the controller 40 receives a first mass concentration value 84 from the optical sensor 36 and compares the first mass concentration value 84 with a first mass concentration threshold value 86. When the controller 40 detects that the first mass concentration value 84 reaches (i.e., is substantially equal to or is greater than) the first mass concentration threshold value 86, the controller 40 adjusts an advancement rate associated with the filter 48. Such adjustment increases the advancement rate associated with the filter advancement mechanism 64, thereby causing the filter advancement mechanism 64 to position the filter to an unused or "clean" portion at a relatively high rate. By advancing the filter 48 at a relatively frequent or high rate when the optical sensor 36 detects a relatively high particulate mass concentration within the fluid sample 28, the filter advancement mechanism 64 minimizes evaporation of particulate matter (i.e., evaporative particle losses) from the filter 48. Minimization of particle losses, in turn, increases the accuracy and precision of the particulate mass concentration measurements produced by the particulate mass monitor 20.

Again, with reference to operation of the mass monitor 20 in accordance with FIG. 2, in step 112 the controller 40 determines a final mass concentration level of particulates within the fluid sample 28 based upon a ratio 44 between the first mass concentration and the second mass concentration.

The controller 40 utilizes the ratio 44 to adjust real-time (i.e., instant) particulate mass concentration measurements taken by the optical sensor 36. When applying the ratio 44 to the instant particulate mass concentration measurement taken by the optical sensor 36, the controller 40 multiplies the ratio 44 and the instant particulate mass concentration from the optical sensor 36 to generate the final mass concentration value. The ratio 44, therefore, calibrates the response of the optical sensor 36 with respect to the particulate mass concentration in a fluid (e.g., air) sample as detected by the mass sensor 38.

In certain cases, however, application of the ratio 44 to the instant particulate mass concentration measured by the optical sensor 36 can produce an inaccurate final mass concentration value. For example, this could occur 1) when an operator first engages the particulate mass monitor 20 and the mass sensor 38 operates for a minimal time period (e.g., approximately 5 minutes), or 2) when the fluid sample 28 contains a relatively low (e.g., near zero) particle concentration. As indicated above, when a mass sensor 38 is used for particulate monitoring over relatively short periods of time (less than a few hours), or in the presence of a relatively low particulate concentration within an air sample, the measurements taken can suffer from statistical noise inherent in mass sensor counting methods. In either case, applying the ratio 44 to the instant particulate mass concentration measured by the optical sensor 36 and based upon particulate mass concentration measurements taken by the mass sensor 38 as described, the controller 40 can calculate an inaccurate final mass concentration value. To avoid inaccuracies due to these characteristics of the mass sensor 38, in one arrangement the controller 40 ignores radiometric measurements taken by the mass sensor 38 when the particulate mass concentration of a fluid sample 28 is relatively low.

Figure 5:
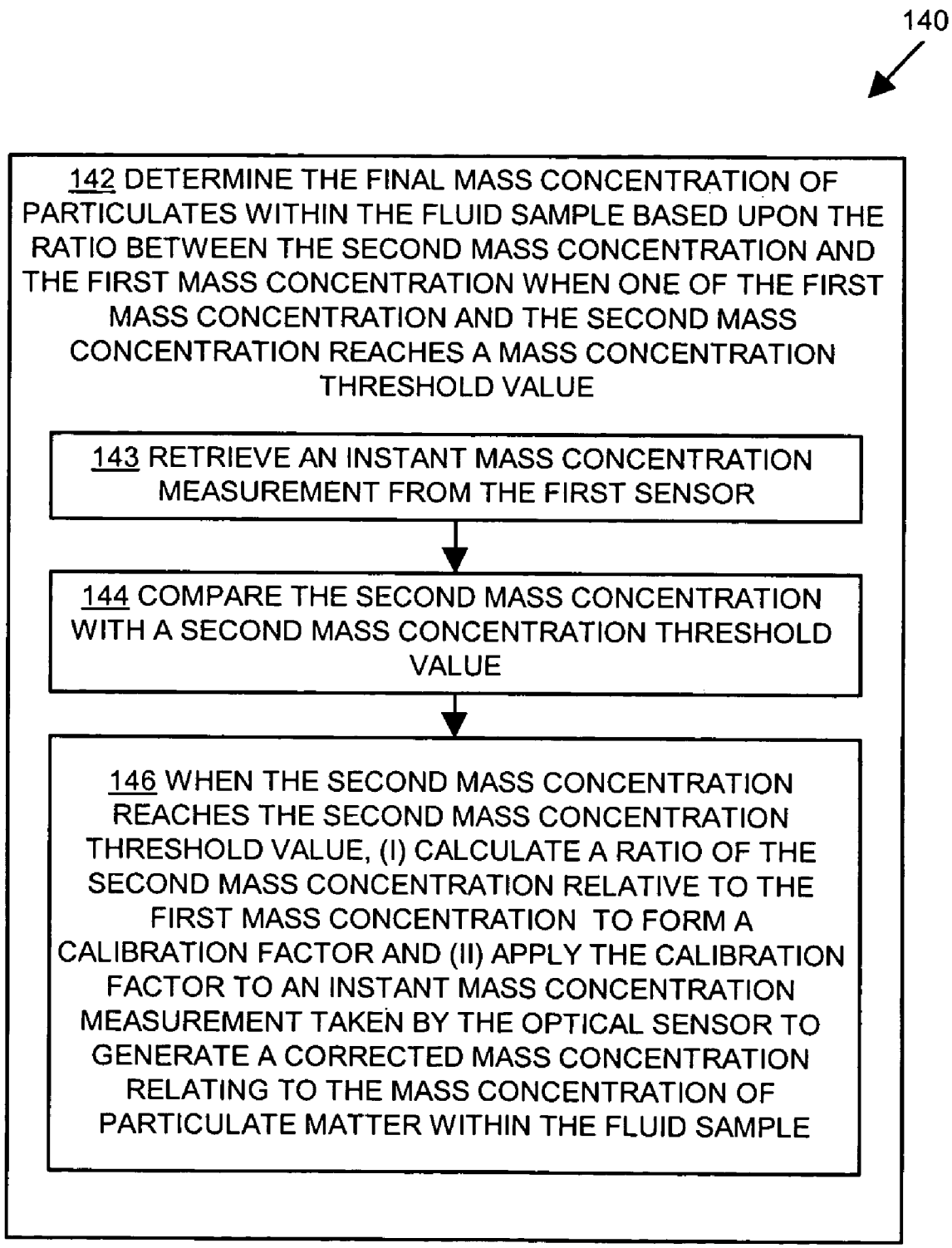
FIG. 5 illustrates a flow chart of a procedure performed by the particulate mass monitor of FIG. 1, according to one embodiment of the invention.

FIG. 5 is a flow chart 140 of a procedure performed by the controller 40 of the particulate mass monitor 20 to account for the inaccuracies in the mass sensor's 38 ability to detect relatively low particulate concentration levels in a fluid sample 28, for example.

In step 142, the controller 40 determines the final mass concentration of particulates within the fluid sample 28 based upon the ratio 44 between the second mass concentration and the first mass concentration when one of the first mass concentration and the second mass concentration reaches a mass concentration threshold value. In one arrangement, the mass concentration threshold value is a minimum concentration detectable by both the optical sensor 36 and the mass sensor 38. The following method steps outline an example of the controller 40 determining the final mass concentration level of particulates within the fluid sample 28.

In step 143, the controller 40 retrieves an instant mass concentration measurement from the first sensor 36. As indicated above, during operation, the optical sensor 36 continuously detects the particulate mass concentration of particulate matter within air 28 entering the particulate mass monitor 20. The controller 40 averages the continuously detected mass concentration measurements taken by the optical sensor 36 over a preset period, such as a period of approximately one minute. The one-minute average particulate mass concentration forms an "instant" mass concentration measurement of the air 28 entering the particulate mass monitor 20.

In step 144, the controller 40 compares the second mass concentration with a second mass concentration threshold value. For example, the controller 40 receives the second mass concentration from the mass sensor 38. If the second mass concentration is less than the second mass concentration threshold value, then the controller 40 does not apply a ratio to correct the instant mass concentration measurement of the optical sensor 36.

In step 146, when the second mass concentration reaches the second mass concentration threshold, the controller 40 first calculates a ratio 44 of the second mass concentration relative to the first mass concentration to form a calibration factor. The controller 40 then applies the calibration factor to an instant mass concentration measurement taken by the optical sensor 36 to generate a corrected mass concentration relating to the mass concentration of particulate matter within the fluid sample 28.

For example, assume second mass concentration threshold value is 3 micrograms per cubic meter. In the case where the second mass concentration is greater than or approximately equal to (i.e., reaches) the second mass concentration threshold value of 3 micrograms per cubic meter, the controller 40 calculates the ratio 44 and applies the ratio 44 to the instant mass concentration measurement taken by the optical sensor 36. However, in certain cases (e.g., the mass sensor 38 operates for a minimal time period or the fluid sample 28 contains a relatively low or near zero particulate concentration), the second mass concentration is less than (i.e., does not reach) the second mass concentration threshold value of 3 micrograms per cubic meter. In those cases, the controller 40 does not apply the ratio 44 to the instant mass concentration measurement taken by the optical sensor 36. Instead, the controller 40 reports to a user, via the output device 72, the instant mass concentration measurement as the final mass concentration level of particulates within the fluid sample 28. Thus, the controller 40 minimizes the effect of potentially inaccurate mass sensor 38 measurements on the instant mass concentration measurements taken by the optical sensor 36, and correspondingly produced by the particulate mass monitor 20.

As indicated above, the controller 40 corrects an output of the optical sensor 36 using a ratio 44 of the second mass concentration, measured using the mass sensor 38, relative to the first mass concentration, measured using the optical sensor 36. The controller 40 uses the ratio 44 to adjust the inaccuracies of particulate mass concentration measurements, made by the optical sensor 36, with the relatively accurate particulate mass concentration measurements of the mass sensor 38. In one arrangement, the controller 40 also uses the ratio 44 to detect the size of the particulates within a fluid sample 28 and correlate the size of the particulates with concentration trends or fluid velocity (e.g., in the case of air, wind velocity) to identify the source of the particulate matter.

Figure 6:
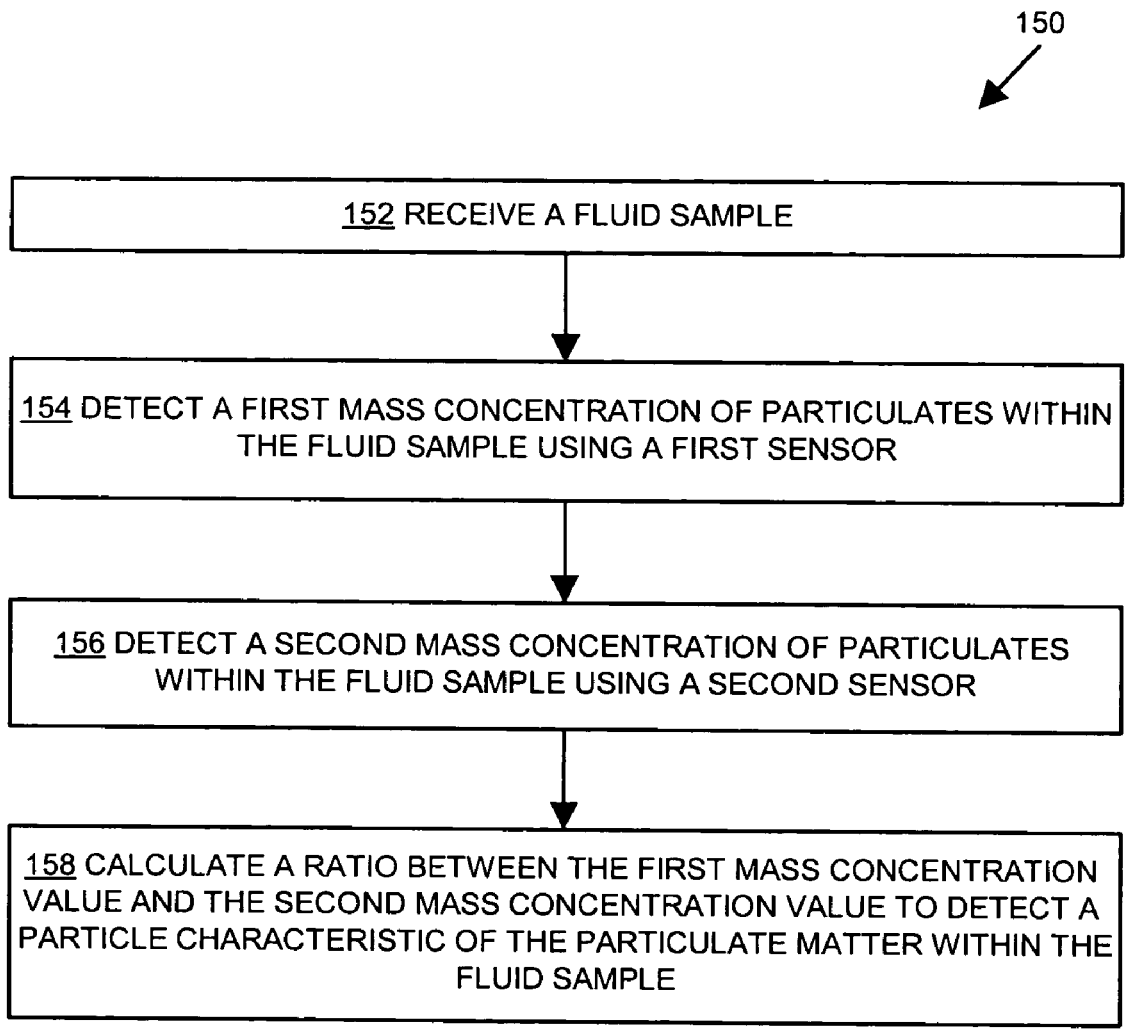
FIG. 6 illustrates a flow chart of a procedure performed by the particulate mass monitor of FIG. 1, according to one embodiment of the invention.

FIG. 6 is a flowchart 150 of a procedure performed by the particulate mass monitor 20 to characterize a particle source for particulate matter within a fluid.

In step 152, the particulate mass monitor 20 receives a fluid sample 28. As indicated above, in one arrangement, the pump 35 generates a pressure differential between the fluid inlet 32 and the fluid outlet 34 to cause the fluid sample 28 to enter the particulate mass monitor 20 via the fluid inlet 32.

In step 154, the controller 40 detects a first mass concentration of particulates within the fluid sample 28 using a first sensor 36. For example, as indicated above, the controller 40 receives an output signal from the optical sensor 36 indicating the mass concentration of particulates (i.e., the first mass concentration of particulates) within the fluid sample 28.

In step 156, the controller 40 detects a second mass concentration of particulates within the fluid sample 28 using a second sensor 38. For example, as indicated above, the controller 40 receives a signal from the mass sensor 38 proportional to the mass concentration of particulates within the fluid sample 28 (i.e., the second mass concentration of particulates).

In step 158, the controller 40 calculates a ratio 44 between the first mass concentration value and the second mass concentration value to detect a particulate characteristic of the particulate matter within the fluid sample 28. For example, for a fluid sample 28 having a substantially constant flow rate, assume the controller 40 continuously calculates (i.e., continuously updates) the ratio 44 between the first mass concentration value and the second mass concentration value of the fluid sample 28 over a time period. Also assume that over the time period, as a result of the continuously updated calculations, the value of the ratio 44 increases and approaches a value of 1. Such an increase in the ratio 44 indicates a change in a particulate size characteristic, such as an increase in the particulate size of the particulates within the fluid sample 28. By detecting an increase in the particulate size, the controller 40 correlates the increase (i.e., the change in particulate characteristic) to a change in the particulate source, such as caused by a change in wind (i.e., fluid flow) direction, and provides a warning to a user, via the output device 72.

Figure 7:
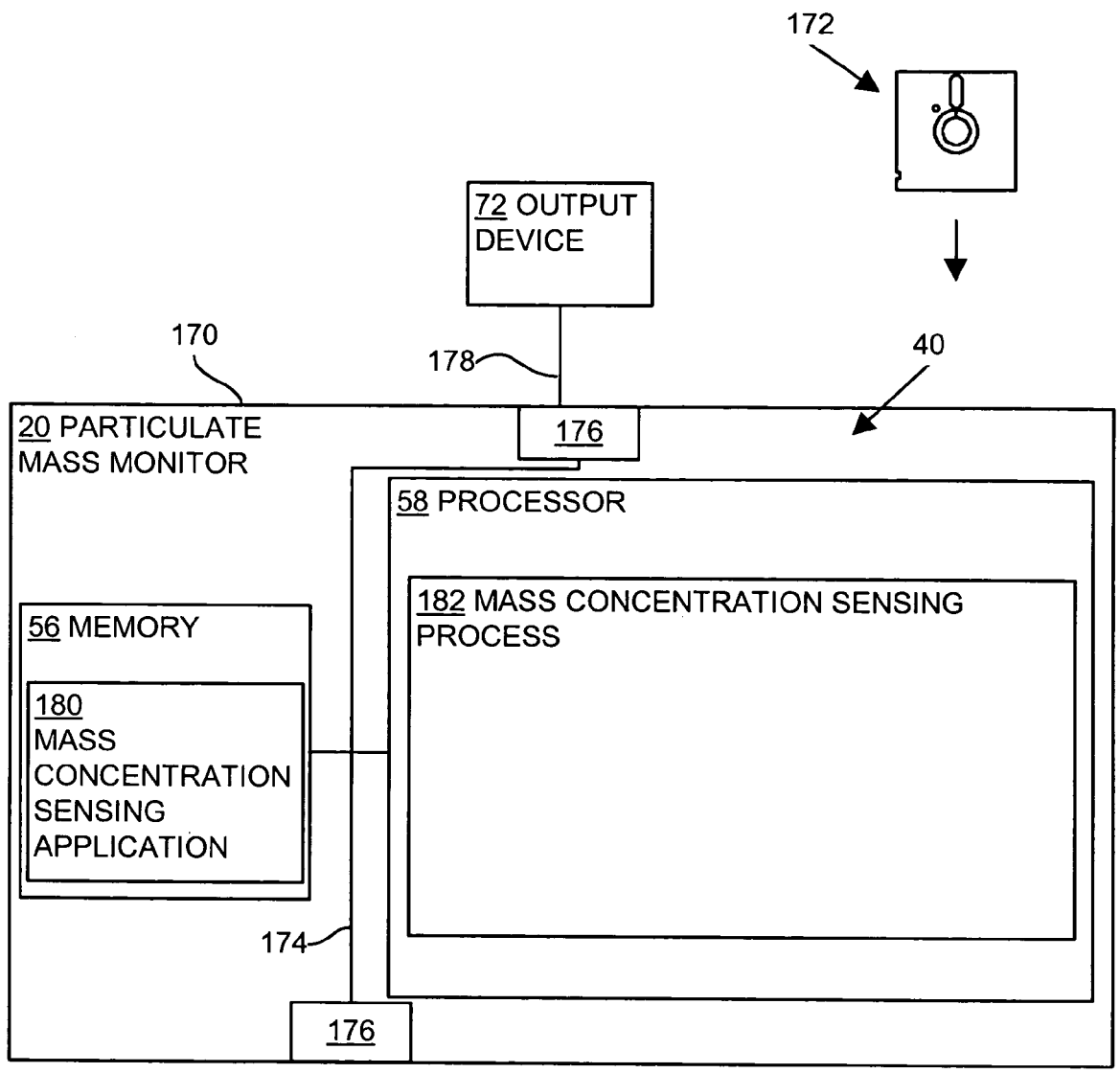
FIG. 7 illustrates a computer device, configured as a particulate mass monitor, according to one embodiment of the invention.

FIG. 7 illustrates a more detailed architecture of a particulate mass monitor 20 configured as a computerized device 170. The computerized device 170 includes a controller 40 formed of a memory 56 and a processor 58. A computer program product 172 includes an application or logic instructions that are loaded into the computer device 170 to configure the device 170 to perform as a particulate mass monitor 20.

The particulate mass monitor 20, in this example, includes an interconnection mechanism 174 such as a data bus and/or other circuitry that interconnects the controller memory 56 and the processor 58, and one or more communications interfaces 176. The communication interface 176 connects with the output device 72 via connections 178.

The memory 56 may be any type of volatile or non-volatile memory or storage system such as computer memory (e.g., random access memory (RAM), read-only memory (ROM), or other electronic memory), disk memory (e.g., hard disk, floppy disk, optical disk and so forth). The memory 56 is encoded with logic instructions (e.g., software code) and/or data that form a mass concentration sensing application 180 configured according to embodiments of the invention. In other words, the mass concentration sensing application 180 represents software code, instructions and/or data that represent or convey the processing logic steps and operations as explained herein and that reside within memory or storage or within any computer readable medium accessible to the particulate mass monitor 20.

The processor 58 represents any type of circuitry or processing device such as a central processing unit, microprocessor or application-specific integrated circuit that can access the mass concentration sensing application 180 encoded within the memory 56 over the interconnection mechanism 174 in order to execute, run, interpret, operate or otherwise perform the mass concentration sensing application 180 logic instructions. Doing so forms the mass concentration sensing process 182. In other words, the mass concentration sensing process 182 represents one or more portions of the logic instructions of the content portion reception application while being executed or otherwise performed by, or in the processor 58 within the particulate mass monitor 20. The particulate mass monitor 20 in FIG. 1 collectively represents either one or both of the mass concentration sensing application 180 and the mass concentration sensing process 182.

While this invention has been particularly shown and described with references to preferred embodiments thereof, it will be understood by those skilled in the art that various changes in form and details may be made therein without departing from the spirit and scope of the invention as defined by the appended claims.

For example, while in FIG. 2 the controller 40 is configured as separate from the mass sensor 38 and from the optical sensor 36, such a configuration is by way of example only. In one arrangement, the controller 40 forms part of either, or both, the mass sensor 38 and the optical sensor 36.

As indicated above, the mass sensor 38 (i.e., a second mass sensor device) is a beta radiation attenuation sensing assembly. Such description is by way of example only. In another arrangement, the second mass sensing detector is a mechanical resonance sensing assembly. For example, the mechanical resonance assembly includes a tensioned filter having a set resonant frequency. The tensioned filter sensor is positioned within the channel between the optical sensor 36 and the fluid outlet 34, for example. As an air sample 28 flows through the tensioned filter, particulate matter within the air sample 28 collects on the filter to increase the mass of the filter and changes the resonant frequency of the filter in proportion to the increase in mass. The controller 40 uses a change in resonant frequency signal from the tensioned filter to determine the particulate mass concentration of the fluid sample over time. Another example of a mechanical resonance mass sensor includes a tensioned metal foil on which the particulate matter is collected by means of electrostatic precipitation using a point-to-plane corona discharge. The controller 40 then uses a change in the resonant frequency of the tensioned metal foil to determine the particulate mass concentration of the fluid sample over time.

As indicated above, the particulate mass monitor 20 includes an optical sensor 36 positioned between the fluid inlet 32 and the mass sensor 38. The mass sensor 38 within the particulate mass monitor 20 is at a position distal to (i.e., downstream from) the optical sensor 36. In such an arrangement, the optical sensor 36 and mass sensor 38 are configured in a sequential or series flow configuration to detect a particulate mass concentration within a common air sample received by the particulate mass monitor 20. Such description is by way of example only.

Figure 8:
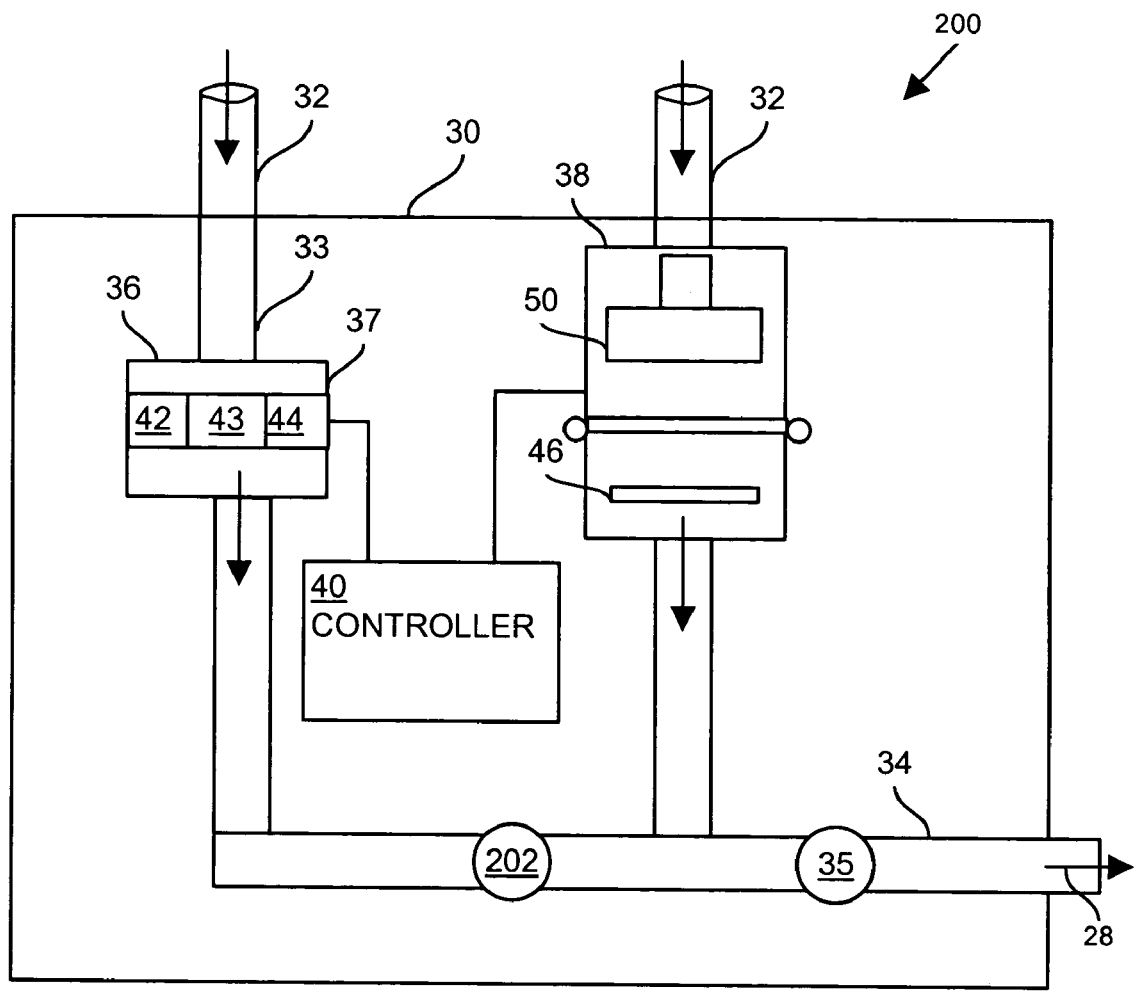
FIG. 8 illustrates an arrangement of a particulate mass monitor, according to one embodiment of the invention.

FIG. 8 illustrates an arrangement of a particulate mass monitor 200 having an optical sensor 36 positioned in parallel relative to a mass sensor 38. In such an arrangement, the optical (i.e., or other fast response) sensor 36 samples air in parallel to the beta attenuation mass (i.e., or other accurate but slow) sensor 38. The signals from the two parallel sampling sensors 36, 38 are then processed in the same manner as in the case of the sequential or series sampling configuration. In one arrangement, the particulate mass monitor 200 includes a valve 202 that allows a user to independently adjust a flow rate from the pump 35 to either the optical sensor 36 or mass sensor 38.

What is claimed is:

1. A method for monitoring a mass concentration of particulates within a fluid comprising:
   receiving a fluid sample;
   detecting a first mass concentration of particulates within the fluid sample using a first sensor;
   detecting a second mass concentration of particulates within the fluid sample using a second sensor; and in response to identifying that at least one of the first mass concentration and the second mass concentration reaches a mass concentration threshold value, determining a final mass concentration level of particulates within the fluid sample based on a mass concentration from the first sensor and a ratio between the second mass concentration and the first mass concentration.

2. The method of claim 1 wherein the step of detecting the first mass concentration comprises:
receiving, in a substantially continuous manner, first mass concentration values of particulates within the fluid sample from the first sensor; and
averaging, in a substantially continuous manner, the first mass concentration values over a time interval to generate a first average mass concentration value of particulates within the fluid sample.

3. The method of claim 2 wherein the step of detecting a second mass concentration comprises:
receiving, in a substantially continuous manner, second mass concentration values of particulates within the fluid sample from the second sensor; and
averaging, in a substantially continuous manner, the second mass concentration values over the time interval to generate a second average mass concentration value of particulates within the fluid sample.

4. The method of claim 3 wherein the step of determining the final mass concentration comprises:
retrieving an instant mass concentration measurement from the first sensor;
calculating a ratio of the second average mass concentration value relative to the first average mass concentration value to form a calibration factor; and
applying the calibration factor to the instant mass concentration to generate the final mass concentration relating to the mass concentration of particulates within the fluid sample.

5. The method of claim 3 wherein the step of detecting a first mass concentration of particulates within the fluid sample further comprises:
detecting a rate of change of the first mass concentration of the fluid sample; and
adjusting the time interval for averaging the first mass concentration of particulates within the fluid sample and for averaging the second mass concentration of particulates within the fluid sample when the rate of change of the first mass concentration reaches a rate threshold.

6. The method of claim 1 further comprising applying heat to the fluid sample based upon a humidity level associated with the fluid sample.

7. The method of claim 6 wherein the step of applying heat to the fluid sample comprises:
detecting a relative humidity level of the fluid sample;
comparing the relative humidity level of the fluid sample with a threshold humidity value; and
when the relative humidity level of the fluid sample reaches the threshold value, heating the fluid sample prior to detecting the second mass concentration of particulates within the fluid sample.

8. The method of claim 7 wherein:
the step of comparing comprises comparing the relative humidity level of the fluid sample with a threshold humidity value of approximately 70% relative humidity; and
when the relative humidity level of the fluid sample reaches approximately 70% relative humidity, heating the fluid sample prior to detecting the second mass concentration of particulates within the fluid sample.

9. The method of claim 1 wherein the step of determining comprises determining the final mass concentration of particulates within the fluid sample based upon the ratio between the second mass concentration and the first mass concentration when at least one of the first mass concentration and the second mass concentration reaches a mass concentration threshold value.

10. The method of claim 9 wherein the step of determining comprises:
retrieving an instant mass concentration measurement from the first sensor;
comparing the second mass concentration with a second mass concentration threshold value; and
when the second mass concentration reaches the second mass concentration threshold value, (i) calculating a ratio of the second mass concentration relative to the first mass concentration to form a calibration factor and (ii) applying the calibration factor to the instant mass concentration measurement to generate a corrected mass concentration relating to the mass concentration of particulate matter within the fluid sample.

11. The method of claim 1 wherein the step of detecting the second mass concentration of particulates within the fluid sample comprises detecting the second mass concentration of particulates within the fluid sample using a beta radiation attenuation sensor.

12. The method of claim 11 further comprising:
comparing the first mass concentration with a first mass concentration threshold value; and
adjusting an advancement rate of a filter associated with the beta radiation attenuation detector in response to the first mass concentration reaching the first mass concentration threshold value.

13. The method of claim 1 wherein the step of detecting the second mass concentration of particulates within the fluid sample comprises detecting the second mass concentration of particulates within the fluid sample using a mechanical resonance sensing assembly.

14. The method of claim 1 wherein the step of detecting the first mass concentration of particulates within the fluid sample comprises measuring the first mass concentration of particulates within the fluid sample using an optical sensor.

15. A particulate mass monitor comprising:
a first sensor configured to receive a fluid sample;
a second sensor configured to receive the fluid sample; and
a controller in electrical communication with the first sensor and in electrical communication with the second sensor, the controller configured to:
detect a first mass concentration of particulates within the fluid sample using the first sensor;
detect a second mass concentration of particulates within the fluid sample using second sensor; and
determine a final mass concentration of particulates within the fluid sample based on a mass concentration from the first sensor and a ratio between the second mass concentration and the first mass concentration; and
wherein the controller is operable to determine the final mass concentration level of particulates within the fluid sample based upon the ratio between the second mass concentration and the first mass concentration when at least one of the first mass concentration and the second mass concentration reaches a mass concentration threshold value.

16. The particulate mass monitor of claim 15 wherein the controller is operable, when detecting the first mass concentration, to:
receive, in a substantially continuous manner, first mass concentration values of particulates within the fluid sample from the first sensor; and
average, in a substantially continuous manner, the first mass concentration values over a time interval to generate a first average mass concentration value of particulates within the fluid sample.

17. The particulate mass monitor of claim 16 wherein the controller is operable, when detecting the second mass concentration, to:
receive, in a substantially continuous manner, second mass concentration values of particulates within the fluid sample from the second sensor; and
average, in a substantially continuous manner, the second mass concentration values over the time interval to generate a second average mass concentration value of particulates within the fluid sample.

18. The particulate mass monitor of claim 17 wherein the controller is operable to retrieve an instant mass concentration measurement from the first sensor and, when determining the final mass concentration, to:
calculate a ratio of the second mass concentration value relative to the first mass concentration value to form a calibration factor; and
apply the calibration factor to the instant mass concentration measurement to generate the final mass concentration relating to the mass concentration of particulates within the fluid sample.

19. The particulate mass monitor of claim 17 wherein the controller is operable, when detecting the first mass concentration of particulates within the fluid sample, to:
detect a rate of change of the first mass concentration of the fluid sample; and
adjust the time interval for averaging the first mass concentration of particulates within the fluid sample and for averaging the second mass concentration of particulates within the fluid sample when the rate of change of the first mass concentration reaches a rate threshold.

20. The particulate mass monitor of claim 15 further comprising a heating element and a humidity detector, the heating element operable to apply heat to the fluid sample based upon a humidity level associated with the fluid sample as measured by the humidity detector.

21. The particulate mass monitor of claim 20 wherein the controller is configured to:
detect a relative humidity level of the fluid sample using the humidity detector;
compare the relative humidity level of the fluid sample with a threshold humidity value; and
when the relative humidity level of the fluid sample reaches the threshold value, heat the fluid sample with the heating element prior to detecting the second mass concentration of particulates within the fluid sample.

22. The particulate mass monitor of claim 21 wherein:
the controller is operable to compare the relative humidity level of the fluid sample with a threshold humidity value of approximately 70% relative humidity; and
when the relative humidity level of the fluid sample reaches approximately 70% relative humidity, the controller is configured to heat the fluid sample with the heating element prior to detecting the second mass concentration of particulates within the fluid sample.

23. The particulate mass monitor of claim 15 wherein the controller is operable to retrieve an instant mass concentration measurement from the first sensor and to:
compare the second mass concentration with a second mass concentration threshold value; and
when the second mass concentration reaches the second mass concentration threshold value, (i) calculate a ratio of the second mass concentration value relative to the first mass concentration value to form a calibration factor and (ii) apply the calibration factor to the instant mass concentration measurement to generate a corrected mass concentration value relating to the mass concentration of particulate matter within the fluid sample.

24. The particulate mass monitor of claim 15 wherein the second sensor comprises a beta radiation attenuation sensor.

25. The particulate mass monitor of claim 24 wherein the controller is operable, when detecting the first mass concentration of particulates within the fluid sample, to:
compare the first mass concentration with a first mass concentration threshold value; and
adjust an advancement rate of a filter associated with the beta radiation attenuation sensor in response to the first mass concentration reaching the first mass concentration threshold value.

26. The particulate mass monitor of claim 15 wherein the second sensor comprises a mechanical resonance sensing assembly.

27. The particulate mass monitor of claim 15 wherein the first sensor comprises an optical sensor.

28. A computer program product having a computer-readable medium including computer program logic encoded thereon that, when performed on a controller provides a method for performing the operations of:
detecting a first mass concentration of particulates within a fluid sample using a first sensor;
detecting a second mass concentration of particulates within the fluid sample using a second sensor;
determining a final mass concentration level of particulates within the fluid sample based on a mass concentration from the first sensor, and a ratio between the second mass concentration and the first mass concentration; and
wherein determining the final mass concentration level includes multiplying an instant value of mass concentration detected by the first sensor by the ratio, wherein the ratio represents a time-averaged mass concentration value detected by the first sensor divided by a time-averaged mass concentration value detected by the second sensor.

29. A method for characterizing a particulate source for particulate matter within a fluid comprising:
receiving a fluid sample;
detecting a first mass concentration of particulates within the fluid sample using a first sensor;
detecting a second mass concentration of particulates within the fluid sample using a second sensor;
calculating a ratio between the first mass concentration value and the second mass concentration value to detect a characteristic of the particulate matter within the fluid sample; and
wherein the step of detecting a first mass concentration of particulates within the fluid sample further comprises:
detecting a rate of change of the first mass concentration of the fluid sample; and
adjusting a time interval for averaging the first mass concentration of particulates within the fluid sample and for averaging the second mass concentration of particulates within the fluid sample when the rate of change of the first mass concentration reaches a rate threshold.

30. The method of claim 29 further comprising correlating the characteristic of the particulate matter with a particulate source.

31. The particulate mass monitor of claim 15 wherein:
the first mass sensor is a high speed mass sensor that detects a mass concentration of particles in a relatively fast manner in comparison to the second mass sensor; and
the second mass sensor is a low speed mass sensor that detects a mass concentration of particles with high accuracy but in a relatively slow manner in comparison to the first mass sensor.

32. The particulate mass monitor of claim 26 wherein the mechanical resonance sensing assembly includes a tensioned filter having a set resonant frequency upon which particulate matter collects to alter the set resonant frequency.

33. The particulate mass monitor of claim 26 wherein the mechanical resonance sensing assembly includes a tensioned metal foil on which the particulate matter is collected by means of electrostatic precipitation using a point-to-plane corona discharge to alter the set resonant frequency.

34. The particulate mass monitor of claim 27 wherein the optical sensor is a nephelometer.

35. A method for monitoring a mass concentration of particulates within a fluid comprising:
receiving a fluid sample;
detecting a first mass concentration of particulates within the fluid sample using a first sensor;
detecting a second mass concentration of particulates within the fluid sample using a second sensor;
determining a final mass concentration level of particulates within the fluid sample based on a mass concentration from the first sensor and a ratio between the second mass concentration and the first mass concentration; and
wherein the step of detecting a first mass concentration of particulates within the fluid sample further comprises:
utilizing the first sensor to detect a rate of change of the first mass concentration of the fluid sample; and
in response to identifying that the rate of change of the first mass concentration reaches a rate threshold value, adjusting a respective time interval for averaging an amount of the first mass concentration of particulates detected by the first sensor.

36. The method of claim 35, further comprising:
in response to identifying that the rate of change of the first mass concentration reaches the rate threshold value, adjusting a respective time duration used for averaging an amount of the second mass concentration of particulates detected by the second sensor.

37. A method for monitoring a mass concentration of particulates within a fluid, the method comprising:
receiving a fluid sample;
detecting a first mass concentration of particulates within the fluid sample using a first sensor;
detecting a second mass concentration of particulates within the fluid sample using a second sensor; and
determining a final mass concentration level of particulates within the fluid sample based on a mass concentration from the first sensor and a ratio between the second mass concentration and the first mass concentration;
wherein the step of determining the final mass concentration level further includes:
retrieving an instant mass concentration measurement from the first sensor;
comparing the second mass concentration with a mass concentration threshold value.

38. The method of claim 37, wherein the step of determining the final mass concentration level further includes:
in response to detecting that the second mass concentration reaches the mass concentration threshold value, initiating operations of: (i) calculating a ratio of the second mass concentration relative to the first mass concentration to form a calibration factor and (ii) applying the calibration factor to the instant mass concentration measurement to generate a corrected mass concentration value indicating a respective mass concentration of particulate matter within the fluid sample.

39. A method for monitoring a mass concentration of particulates within a fluid, the method comprising:
receiving a fluid sample;
detecting a first mass concentration of particulates within the fluid sample using a first sensor;
detecting a second mass concentration of particulates within the fluid sample using a second sensor;
determining a final mass concentration level of particulates within the fluid sample based on a mass concentration from the first sensor and a ratio between the second mass concentration and the first mass concentration; and
wherein determining the final mass concentration level includes multiplying an instant value of mass concentration detected by the first sensor by the ratio, wherein the ratio represents a time-averaged mass concentration value detected by the first sensor divided by a time-averaged mass concentration value detected by the second sensor.

40. The method of claim 39, further comprising:
repeatedly updating the ratio over a sampling time to provide a running correction for purposes of determining the final mass concentration level of particulates within the fluid sample.

41. The method as in claim 1 further comprising:
in response to identifying that the second mass concentration level as detected by the second sensor over a duration of time is less than a given threshold value, ignoring use of the ratio and report that an instant mass concentration value sensed by the first sensor as a respective mass concentration level of particulates in the fluid sample.

* * * * *